(12) United States Patent
El-Habnouni et al.

(10) Patent No.: US 11,351,096 B2
(45) Date of Patent: Jun. 7, 2022

(54) ORGANIC COMPOUNDS

(71) Applicant: GIVAUDAN SA, Vernier (CH)

(72) Inventors: Sarah El-Habnouni, Singapore (SG); Emmanuel Aussant, Paris (FR); Vladica Bocokic, Rueil-Malmaison (FR); Sandra Guinebretiere, Franconville (FR); Florent Robert, Fontenay sous Bois (FR)

(73) Assignee: GIVAUDAN SA, Vernier (CH)

( * ) Notice: Subject to any disclaimer, the term of this patent is extended or adjusted under 35 U.S.C. 154(b) by 0 days.

(21) Appl. No.: 16/968,284

(22) PCT Filed: Mar. 6, 2019

(86) PCT No.: PCT/EP2019/055484
§ 371 (c)(1),
(2) Date: Aug. 7, 2020

(87) PCT Pub. No.: WO2019/174978
PCT Pub. Date: Sep. 19, 2019

(65) Prior Publication Data
US 2021/0030639 A1   Feb. 4, 2021

(30) Foreign Application Priority Data
Mar. 14, 2018  (GB) ..................... 1804038

(51) Int. Cl.
*A61K 8/11* (2006.01)
*A61K 8/06* (2006.01)
*A61K 8/84* (2006.01)
*A61Q 13/00* (2006.01)

(52) U.S. Cl.
CPC .............. *A61K 8/11* (2013.01); *A61K 8/068* (2013.01); *A61K 8/84* (2013.01); *A61Q 13/00* (2013.01); *A61K 2800/10* (2013.01); *A61K 2800/21* (2013.01); *A61K 2800/412* (2013.01); *A61K 2800/5422* (2013.01); *A61K 2800/5424* (2013.01); *A61K 2800/5426* (2013.01); *A61K 2800/56* (2013.01); *A61K 2800/594* (2013.01)

(58) Field of Classification Search
CPC ............ A61K 8/068; A61K 8/84; A61K 8/11; A61K 2800/56; A61K 2800/5426; A61K 2800/21; A61K 2800/5424; A61K 2800/5422; A61K 2800/10; A61K 2800/594; A61K 2800/412; A61Q 13/00
See application file for complete search history.

(56) References Cited

U.S. PATENT DOCUMENTS

| 5,342,556 | A | 8/1994 | Helmut et al. | |
|---|---|---|---|---|
| 2013/0089590 | A1* | 4/2013 | Hotz | A61K 8/92 424/401 |
| 2013/0196071 | A1* | 8/2013 | Yang | C08G 18/703 427/386 |
| 2015/0140050 | A1 | 5/2015 | Hotz et al. | |

FOREIGN PATENT DOCUMENTS

| DE | 4130743 A1 | 3/1993 | |
|---|---|---|---|
| EP | 2399667 A1 | 12/2011 | |
| WO | 2011161229 A1 | 12/2011 | |
| WO | 2016071151 A1 | 5/2016 | |
| WO | WO-2016207180 A1 * | 12/2016 | ............. C08G 12/32 |
| WO | 2017085105 A1 | 5/2017 | |
| WO | 2018050914 A1 | 3/2018 | |

OTHER PUBLICATIONS

International Search Report and Written Opinion of the International Searching Authority for corresponding application PCT/EP2019/055484 dated Jun. 26, 2019.
GB Search Report for corresponding application GB 1804038.6 dated Aug. 14, 2018.

* cited by examiner

*Primary Examiner* — Doan T Phan
(74) *Attorney, Agent, or Firm* — Norris McLaughlin PA

(57) ABSTRACT

Disclosed is a process for preparing an encapsulated fragrance composition. The composition comprises a plurality of microcapsules dispersed in a dispersion medium. The microcapsules comprise a core and a shell around the core. The process comprises the consecutive steps of:
  a) Providing an aqueous phase (I) comprising at least one anionically modified polyisocyanate (A);
  b) Providing an organic phase (II) comprising at least one fragrance ingredient;
  c) Mixing the aqueous phase (I) and the an organic phase (II) to obtain a mixture;
  d) Forming an emulsion comprising droplets of the organic phase (II) in the continuous aqueous phase (I);
  e) Adding at least one polyfunctional amine;
  f) Effecting formation of shells around the droplets formed in step d), to obtain a dispersion of microcapsules.
The process comprises the additional step of adding a polyisocyanate (B), which is different from polyisocyanate (A).

19 Claims, No Drawings

ORGANIC COMPOUNDS

This is an application filed under 35 USC 371 based on PCT/EP2019/055484, filed 6 Mar. 2019, which in turn is based on GB 1804038.6 filed 14 Mar. 2018. The present application claims the full priority benefit of these prior applications and herein incorporates by reference the full disclosures of these prior applications.

The present invention relates to a process for preparing an encapsulated fragrance composition, to a use of an anionically modified polyisocyanate as a dispersion aid in such a process and to an encapsulated fragrance composition obtainable by such a process.

It is known to employ encapsulated fragrances in consumer products, such as household care, personal care and fabric care products. Microcapsules are particularly suitable for this purpose. Typically, a microcapsule comprises of a core and a shell around the core, wherein the core comprises at least one fragrance ingredient and the shell is impervious or partially impervious for the core. Microcapsules generally have a volume average diameter from 0.1 µm to 1000 µm. A multitude of shell materials is known for producing such microcapsules. Depending on the type of shell-forming material, and the production process, microcapsules are formed in each case with different properties, such as diameter, size distribution, physical and/or chemical properties.

Fragrance compositions are encapsulated for a variety of reasons. Microcapsules can isolate and protect fragrance ingredients from external suspending media, such as consumer product bases, in which they may be incompatible or unstable. They are also used to assist in the deposition of fragrance ingredients onto substrates, such as skin, hair, fabrics or hard surfaces. Microcapsules can also act as a means for controlling the spatio-temporal release of a fragrance.

Polyurea core-shell microcapsules obtained by reaction of isocyanates with amines are well known in the art. For instance, WO 2011/160733 A1 describes a process for producing microcapsules, wherein the capsule shell is obtained by reaction of two structurally different isocyanates in emulsion form.

Although such microcapsules have proved effective in fragrance delivery, their production is still resource-intensive, not only with respect to materials required, but also regarding plant equipment and personnel. This relatively high resource consumption is also not optimal from an ecological point of view.

Another drawback of polyurea microcapsules of the above-mentioned kind is that they still show a relatively high leakage in extractive media.

It is therefore a problem underlying the present invention to overcome the above-mentioned shortcomings in the prior art.

In particular, it is a problem underlying the present invention to provide a process for preparing an encapsulated fragrance composition, which is operationally simpler and more efficient. Furthermore, the process should be inexpensive and sustainable. With respect to their characteristics in application, the microcapsules produced should be comparable or even superior to known ones. In particular, the microcapsules are supposed to show a reduced leakage in extractive media.

These problems are solved by a process for preparing an encapsulated fragrance composition according to claim 1. The composition comprises a plurality of microcapsules dispersed in a dispersion medium. The microcapsules comprise a core and a shell around the core. The process comprises the consecutive steps of:
  a) Providing an aqueous phase (I) comprising at least one anionically modified polyisocyanate (A);
  b) Providing an organic phase (II) comprising at least one fragrance ingredient;
  c) Mixing the aqueous phase (I) and the an organic phase (II) to obtain a mixture;
  d) Forming an emulsion comprising droplets of the organic phase (II) in the continuous aqueous phase (I);
  e) Adding at least one polyfunctional amine;
  f) Effecting formation of shells around the droplets formed in step d), to obtain a dispersion of microcapsules.

The process comprises the additional step of:
  Adding a polyisocyanate (B), which is different from polyisocyanate (A).

The above-mentioned process allows adding polyisocyanate (A) as well as polyisocyanate (B) directly to the reaction system, i.e. without previously forming a mixture with the organic phase (II). The process according to the present invention is therefore operationally simpler and more efficient, in particular with respect to cost, than those known in the prior art. In particular, the process can be carried out in only one mixing vessel. Additional vessels for preparing pre-mixtures of the polyisocyanates with the organic phase (II) are not required. Especially in industrial production this is a significant advantage, as occupation and cleaning of production equipment is avoided. This leads to higher production capacities and better sustainability, while the production cost are reduced.

Furthermore, in context of the present invention, it has been discovered that anionically modified polyisocyanate (A) can act as a dispersion aid. Dispersion aids ensure that an emulsion comprising droplets of the organic phase (II) in the continuous aqueous phase (I) is formed, which is suitable for formation of shells around the droplets to afford the desired capsules. With the dispersion aids several parameters are controlled, such as the stability of the emulsion and the size of the droplets. They also ensure that the reaction partners for shell formation are present at the phase interface in high concentration. Dispersion aids also prevent a clumping together (agglomeration, coagulation, flocculation) of the emulsified, suspended or dispersed components.

In principle, in a process according to the present invention, no additional dispersion aid is required, which is a further advantage. In order to avoid any ambiguity, however, it is pointed out that in such a process an additional dispersion aid different from anionically modified polyisocyanate (A) can be added, as discussed further herein below. Even when an additional dispersion aid is used in combination with the anionically modified polyisocyanate (A), there is still the advantage that its amount can be reduced.

It has been found that microcapsules produced according to the present invention are comparable or even superior to known ones with respect to their characteristics in application, in particular regarding leakage and fragrance release properties.

In the context of the present invention, an "aqueous phase" is to be understood as the continuous, homogeneous part of a heterogeneous system, (e.g. the mixture obtained in step c), the emulsion formed in step d) or the dispersion formed in step f)) that has as solvent water or a mixture of water with at least one water-miscible organic solvent.

The aqueous phase (I) can have a pH in the range of from 5 to 12, preferably from 7 to 10, for example around 8 or 9.

The pH can be adjusted using an inorganic base, for example sodium hydroxide solution, or carbonate buffer salts.

In the context of the present invention, an "organic phase" is to be understood as the part of a heterogeneous system that is immiscible with water, and in particular with the aqueous phase. The organic phase (II) is generally in liquid form. Preferably, the organic phase (II) contains no or only a minor amount of solid components. In the sense of the present invention, a minor amount means that the amount of solid components is at the most 5% by weight, preferably at the most 1% by weight, more preferably at the most 0.1% by weight, based on the total weight of organic phase (II). In particular, organic phase (II) contains no solid components. The organic phase (II) generally consists of components which have only limited solubility in water. This includes hydrophobic components that are liquid under the encapsulation conditions and mixtures of hydrophobic components, wherein these mixtures are liquid under the encapsulation conditions.

In context of the present invention, the organic phase (II) contains no or only a minor amount of polyisocyanate. Presently, "a minor amount of polyisocyanate" means that the total amount of any polyisocyanates is at the most 5% by weight, preferably at the most 1% by weight, more preferably at the most 0.1% by weight, even more preferably at the most 0.01% by weight, based on the total weight of organic phase (II). In particular, organic phase (II) contains no polyisocyanate.

In step d), an emulsion is formed comprising droplets of the organic phase (II) in the continuous aqueous phase (I). In order to form a stable emulsion, it is preferred to add organic phase (II) on top of aqueous phase (I).

The aqueous phase (I) and organic phase (II) can be emulsified by methods known to the person skilled in the art, e.g. by introducing energy into the mixture through stirring using a suitable stirrer until the mixture emulsifies. The emulsion formed in step d) is preferably prepared by stirring. The rate of stirring can be adjusted to influence the size of droplets of the organic phase (II) in the aqueous phase (I). After a period of vigorous stirring, an emulsion can be obtained, in which the organic phase (II) is dispersed as tiny droplets in the aqueous phase (I). Preferred stirrers are a MIG stirrer, a propellers stirrer, a paraviscs stirrer, an INTERMIG stirrer and an isojet stirrer.

It has been found favorable if the mixture of the aqueous phase (I) and the organic phase (II) in step d) is stirred with a speed of the stirrer of 200 rpm to 1200 rpm, preferably 400 to 800 rpm, in particular for a 1-2 L vessel. Those values are especially favorable if a propeller stirrer is used. The mixture in step d) is stirred for 1 to 120 minutes, preferably 2 minutes to 60 minutes, especially 5 to 30 minutes. The person skilled in the art will understand that such stirring conditions may change depending on the size of the reactor and on the volume of the mixture, also on the exact geometry of the stirrer, and on the ratio of the diameter of the stirrer to the diameter of the reactor. For example, for a Mig stirrer with stirrer to reactor diameter ratio from 0.5 to 0.9 and volumes ranging from 0.5 to 8 tons, the preferable agitation speed in the context of the present invention is from 150 rpm to 50 rpm.

In order to avoid any ambiguity, in context of the present invention, polyisocyanate (B) can be added in neat form or as a mixture, in particular a solution. In any case, polyisocyanate (B) is added separately from the organic phase (II). Preferably, polyisocyanate (B) is added in neat form.

Polyisocyanate (B) can be added to the aqueous phase (I) provided in step a).

Polyisocyanate (B) can be added during step c).
Polyisocyanate (B) can be added to mixture obtained in step c).
Polyisocyanate (B) can be added after step c) and before step d).
Polyisocyanate (B) can be added during step d).
Polyisocyanate (B) can be added after step d) and before step e).
Polyisocyanate (B) can be added after step e) and before step f).

It is preferred to add polyisocyanate (B) during or after step c) and/or during step d). Without being bound by theory, it is surmised that delivery of polyisocyanate (B) to the face interface, where it takes part in shell formation, is then most efficient. Furthermore, the formation of precipitates in the continuous aqueous phase (I) is avoided this way.

For providing an aqueous phase (I) comprising at least one anionically modified polyisocyanate (A) in step a), polyisocyanate (A) can also be added to the aqueous mixture or water either in neat form or as a mixture, preferably in neat from.

Organic isocyanates are compounds in which an isocyanate group is bonded to an organic residue (R—N═C═O or R—NCO). In the context of the present invention, polyisocyanates (or polyfunctional isocyanates) are organic isocyanates with two or more (e.g. 3, 4, 5, etc.) isocyanate groups in a molecule. Suitable polyisocyanates are, for instance, aromatic, alicyclic or aliphatic.

Anionically modified polyisocyanates comprise at least two isocyanate groups and at least one functional group which is anionic or anionogenic. An "anionogenic functional group" is a group which can become anionic depending on the chemical environment, for instance the pH. Suitable anionic or anionogenic groups are, for instance, carboxylic acid groups, sulfonic acid groups, phosphonic acid groups and salts thereof.

Anionically modified polyisocyanate (A) can comprise one or more sulfonic acid groups or salts thereof. Suitable salts can be sodium, potassium or ammonium salts. Ammonium salts are preferred.

Preferably, anionically modified polyisocyanate (A) is obtained by reaction of a polyisocyanate with 2-(cyclohexylamino)-ethanesulfonic acid and/or 3-(cyclohexylamino)-propanesulfonic acid.

More preferably, anionically modified polyisocyanate (A) is obtained by reaction of a polyisocyanate with 2-(cyclohexylamino)-ethanesulfonic acid and/or 3-(cyclohexylamino)-propanesulfonic acid, wherein the polyisocyanate is selected from hexamethylene diisocyanate, tetramethylene diisocyanate, isophorone diisocyanate, dicyclohexylmethane-4,4'-diisocyanate, 2,4- and 2,6-toluylene diisocyanate and isomer mixtures thereof, diphenylmethane diisocyanates, biurets, allophanates and/or isocyanurates of the before-mentioned polyisocyanates.

Anionically modified polyisocyanate (A) can be selected in each case from anionically modified hexamethylene diisocyanate, isophorone diisocyanate, dicyclohexylmethane-4,4'-diisocyanate, the isocyanurate of hexamethylene diisocyanate and mixtures thereof.

Preferably, anionically modified polyisocyanate (A) has:
an average isocyanate functionality of at least 1.8,
a content of isocyanate groups (calculated as NCO; molecular weight=42) of 4.0 to 26.0 wt %,
a content of sulfonate groups (calculated as $SO_3$; molecular weight=80) of 0.1 to 7.7 wt % and
optionally a content of ethylene oxide units bonded within polyether chains (calculated as $C_2H_2O$; molecular weight=44) of 0 to 19.5 wt %, wherein the polyether chains contain a statistical average of 5 to 55 ethylene oxide units.

In particular, anionically modified polyisocyanate (A) can be selected from an anionically modified hexamethylene diisocyanate, an anionically modified hexamethylene diisocyanate, an anionically modified isocyanurate of hexamethylene diisocyanate and mixtures thereof.

In a particularly preferred embodiment, anionically modified polyisocyanate (A) can be according to Formula (1).

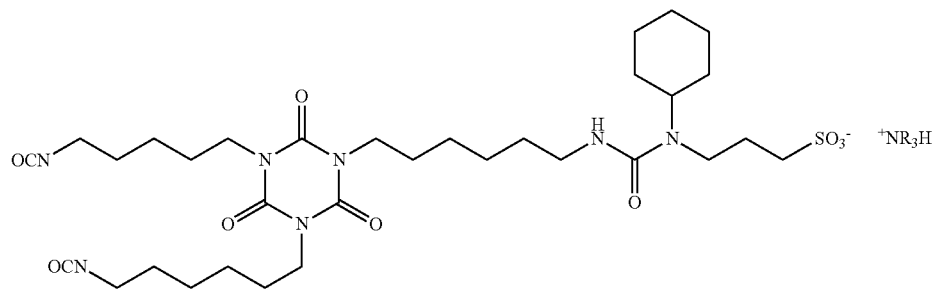

Formula (1)

Formula (1) shows a commercially available anionically modified polyisocyanate, which is a modified isocyanurate of hexamethylene diisocyanate, sold by Covestro under the trademark Bayhydur® XP2547.

In a process according to the present invention, the aqueous phase (I) provided in step a) can additionally comprise a dispersion aid different from anionically modified polyisocyanate (A), in particular a non-ionic dispersion aid.

Dispersion aids that are different from anionically modified polyisocyanates and especially useful in the context of the present invention may be selected from the group consisting of partially hydrolyzed poly(vinyl acetates), such as poly(vinyl alcohols), in particular having a degree of hydrolysis between 80% and 99%, preferably 88% to 96%, poylvinylpyrrolidone (also known as poly(1-vinylpyrrolidin-2-one)), and poly (sodium4-styrenesulfonate).

In a preferred embodiment of the present invention, the dispersion aid different from anionically modified polyisocyanate (A) is polyvinylpyrrolidone (PVP) having a K-value of more than 40, preferably 60 and a molecular weight of more than 150'000 g/mol, preferably from 350'000 to 500'000 g/mol.

The K-values assigned to various grades of PVP polymer represent a function of the average molecular weight, the degree of polymerization and the intrinsic viscosity. The K-values are derived from viscosity measurements and are calculated according to Fikentscher's formula (see for example M. Alger, Polymer Science Dictionary, Chapman & Hall, 1997, page 196).

PVP polymers with lower K-values have molecular weight that are too low to provide an efficient dispersion, while PVP that have higher K-values increase the viscosity of both emulsion and microcapsule slurry to a too large extent.

The dispersion aid different from anionically modified polyisocyanate (A) can be present in an amount of 0.5 to 10% by weight of the aqueous phase (I), preferably 5% by weight of the aqueous phase.

In a process according to the present invention, the aqueous phase (I) provided in step a) can have a surface tension of less than 70 mN/m and preferably less than 60 mN/m. In particular, the aqueous phase (I) provided in step a) can have a surface tension of 35-65 mN/m, 40-60 mN/m or 45-57 mN/m.

An aqueous phase having a low surface tension is more suitable as dispersion medium for an organic phase than an aqueous phase having surface tension close to that of pure water. If the aqueous phase has a lower surface tension, the energy required to provide efficient emulsification is lower and the stability of the emulsion is higher. The surface tension can be measured by using the so-called pendant drop method, for instance with a Drop Shape Analyzer-DSA30 manufactures by Krüss GmbH, Hamburg, Germany.

In a process according to the present invention, polyisocyanate (B) can be a non-ionic polyisocyanate.

The non-ionic polyisocyanate can be selected from the group consisting of 1,6-diisocyanatohexane, 1,5-diisocyanato-2-methylpentane, 1,5-diisocyanato-3-methylpentane, 1,4-diisocyanato-2,3-dimethylbutane, 2-ethyl-1,4-diisocyanatobutane, 1,5-diisocyanatopentane, 1,4-diisocyanatobutane, 1,3-diisocyanatopropane, 1,10-diisocyanatodecane, 1,2-diisocyanatocyclobutane, bis(4-isocyanatocyclohexyl)methane, 3,3,5-trimethyl-5-isocyanatomethyl-1-isocyanatocyclohexane, isophorone diisocyanate (IPDI), hexamethylene 1,6 diisocyanate (HDI), hydrogenated 4,4 diphenyl methane diisocyanate (HMDI).

Polyisocyanate (B) can also be a non-ionic oligomer based on the above-mentioned isocyanate monomers, such as for example the homopolymer of 1,6-diisocyanatohexane. All those monomers and oligomers are sold under the trade name Desmodur® by Covestro AG.

Preferably, non-ionic polyisocyanate (B) is selected from hexamethylene diisocyanate, tetramethylene diisocyanate, dicyclohexylmethane-4,4'-diisocyanate, 2,4- and 2,6 toluylene diisocyanate and isomer mixtures thereof, 2,4'- and 4,4'-diphenylmethane diisocyanate and isomer mixtures thereof, xylylene diisocyanate (for example Desmodur® quix 175 sold by Covestro), optionally as a trimethylolpropane (TMP) adduct (for example commercially available under the trademark Takenate™ D-110N), the biurets, allophanates and/or isocyanurates of the afore-mentioned polyisocyanates or mixtures thereof.

A preferred commercially available non-ionic polyisocyanate (B) is dicyclohexylmethane diisocyanate, in particular sold by Covestro AG under the trademark Desmodur® W1.

A preferred commercially available non-ionic polyisocyanate (B) is hexamethylene diisocyanate, in particular sold by Covestro AG under the trademark Desmodur® N3200.

A preferred commercially available non-ionic polyisocyanate (B) is isophorone diisocyanate, in particular sold by Covestro AG under the trademark Desmodur® Z.

These polyisocyanates have the advantage of being non-aromatic and therefore more sustainable and less prone to oxidation, while still having high reactivity with polyamines and suitable molecular structure for the formation of impervious encapsulating resins.

In a preferred embodiment of the present invention, the anionically modified polyisocyanate (A) is selected from anionically modified hexamethylene diisocyanate, anionically modified isophorone diisocyanate, anionically modified dicyclohexylmethane-4,4'-diisocyanate, the anionically modified isocyanurate of hexamethylene diisocyanate and mixtures thereof and the non-ionic polyisocyanate (B) is selected from hexamethylene diisocyanate, isophorone diisocyanate, dicyclohexylmethane-4,4' diisocyanate, the isocyanurate of hexamethylene diisocyanate and mixtures thereof.

The weight ratio of anionically modified polyisocyanate (A) to non-ionic polyisocyanate (B) can be in the range from 10:1 to 1:10, more preferably in the range from 1:1 to 1:5 and in particular in the range from 1:2 to 1:4. These weight ratios provide resins having the highest imperviousness and therefore the most suitable for encapsulation.

Besides the isocyanates (A) and (B), further isocyanates can additionally be used in the process according to the present invention. For example, adding aromatic polyisocyanates may increase the imperviousness of the resin, if required, whereas adding polyisocyanates having different chemical structures may allow tailoring the mechanical properties of the resins, for example.

The further isocyanates can be selected from the group consisting of compounds with 2 to 5 isocyanate groups, isocyanate prepolymers with an average number of from 2 to 5 isocyanate groups and mixtures thereof. These include, for example, aliphatic, cycloaliphatic and aromatic di-, tri- and higher polyisocyanates.

Preferably, the further polyisocyanate is selected from hexamethylene diisocyanate (HDI), tetramethylene diisocyanate, ethylene diisocyanate, 1,2-diisocyanatododecane, 4-isocyanatomethyl-1,8-octamethylene diisocyanate, triphenylmethane-4,4',4"-triisocyanate, 1,6-diisocyanato-2,2,4-trimethylhexane, 1,6-diisocyanato-2,4,4-trimethylhexane, isophorone diisocyanate (=3-isocyanatmethyl-3,5,5-trimethylcyclohexylisocyanat, 1-isocyanato-3-isocyanatomethyl-3,5,5-trimethylcyclohexan, IPDI), 2,3,3-trimethylhexamethylene diisocyanate, 1,4-cyclohexylene diisocyanate, 1-methyl-2,4-diisocyanatocyclohexane, dicyclohexylmethane-4,4'-diisocyanate (=methylene-bis(4-cyclohexylisocyanate)), 1,3-phenylene diisocyanate, 1,4-phenylene diisocyanate, 2,4- and 2,6-toluylene diisocyanate and isomer mixtures thereof, 1,5-naphthylene diisocyanate, 2,4'- and 4,4'-diphenylmethane diisocyanate (MOi), mixtures of diphenylmethane diisocyanates and more highly polycyclic homologs of diphenylmethane diisocyanate (polymeric MDI), hydrogenated 4,4'-diphenylmethane diisocyanate (H12MDI), xylylene diisocyanate (XDI), 1,3-bis(isocyanatomethyl)cyclohexane, 1,4-bis(isocyanatomethyl)cyclohexane tetramethylxylol diisocyanate (TMXDI), 4,4'-dibenzyl diisocyanate, 4,4'-diphenyldimethylmethane diisocyanate, di- and tetraalkyldiphenylmethandiisocyanates, dimer fatty acid diisocyanates, chlorinated and brominated diisocyanates, 4,4' diisocyanatophenylperfluoroethane, tetramethoxybutane-1,4-diisocyanate, phosphorus-containing diisocyanates, sulfur-containing diisocyanares, anionically modified polyisocyanates, polyethylene oxide-containing isocyanate, oligomers of the afore-mentioned polyisocyanates that contain urethane, allophanate, isocyanurate, uretdione, carbodiimide or biuret groups, and mixtures thereof.

Suitable chlorinated and brominated polyisocyanates comprise polyisocyanates with reactive halogen atoms. Preferably, the chlorinated and brominated polyisocyanate is selected from 1-chloromethylphenyl-2,4-diisocyanate, 1-bromomethylphenyl-2,6-diisocyanate, 3,3-bischloromethylether and 4,4'-diphenyldiisocyanate.

Suitable sulfur-containing polyisocyanates are obtained, for example, by reacting 2 mol of hexamethylene diisocyanate with 1 mol of thiodiglycol or dihydroxydihexyl sulfide.

In context of the present invention, the term "polyfunctional amine" denotes amines that comprise at least two groups capable of reacting with NCO groups, wherein at least one of the groups capable of reacting with NCO groups is a primary or secondary amino group. When the polyfunctional amine contains only one primary or secondary amino group, it will contain one or more additional functional groups that are capable of reacting with NCO groups in a polymerisation reaction. The groups of the polyfunctional amines that are reactive toward NCO groups are preferably chosen from hydroxyl groups and primary or secondary amino groups. Reaction of NCO groups with amino groups leads to the formation of urea groups. Reaction of NCO groups with OH groups leads to the formation of urethane groups. However, the reaction with OH groups often requires a catalyst. The amount of polyfunctional amines, which is introduced, is usually in a molar excess relative to the stoichiometric amount needed to convert the free isocyanate groups.

The polyfunctional amine is preferably selected from diamines, triamines, tetramines, and higher order polyfunctional amines, aminoalcohols, melamines, urea, hydrazines, polymeric polyamines, and mixtures thereof.

Suitable diamines are, for example, 1,2-ethylenediamine, 1,3-propylenediamine, 1,4 diaminobutane, 1,5-diaminopentane, 1,6-diaminohexane, 1,3-diamino-1-methylpropane, 1,4-diaminocyclohexane, piperazin or mixtures thereof.

Suitable amino alcohols are, for example, 2-aminoethanol, 2-(N-methylamino)ethanol, 3-aminopropanol, 4-aminobutanol, 1-ethylaminobutan-2-ol, 2-amino-2-methyl-1-propanol, 4 methyl-4-aminopentan-2-ol or mixtures thereof.

Suitable polymeric polyamines are in principle linear or branched polymers that have at least two primary or secondary amino groups. Additionally, these polymers can have tertiary amino groups in the polymer chain.

The polymeric polyamine is preferably selected from polyalkyleneamines, polyvinylamines, polyetheramines and mixtures thereof. More preferably, the polymeric polyamine is selected from polyalkyleneimines, in particular polyethyleneimines.

Preference is given to polymeric polyamines having a weight-average molecular weight of at least 300 g/mol. More preferred are polymeric polyamines having a weight-average molecular weight of from 500 to 2 000 000 g/mol, in particular from 700 to 1 000 000 g/mol, even more particularly from 800 to 500 000 g/mol.

In a preferred embodiment, the polyfunctional amine comprises or consists of at least one polyethyleneimine.

Polyethyleneimines may be short chain polyethyleneimines with the general formula $H_2N(CH_2CH_2NH)_nH$, wherein n is an integer >1 (n=2: diethylenetriamine; n=3; triethylenetetramine; n=4: tetraethylenepentamine). These are sometimes called polyethyleneamines or polyalkylenepolyamines. Polyethyleneimines may also be long chain polyethyleneimines.

In the processes according to the present invention, polyethyleneimines with a molecular weight of at least 500 g/mol, preferably from 600 to 30 000 or 650 to 25 000 g/mol and in particular from 700 to 10 000 g/mol or 850 to 5000 g/mol, are preferably used.

The polyfunctional amine can be a polyethyleneimine containing the following repeat units

wherein
x is from 8 to 1500, preferably from 10 to 1000;
y is from 0 to 10, preferably from 0 to 5, especially 0;
z is 2+y.

With these polyethyleneimines good results could be achieved, in particular with respect to leakage in extractive media.

Preferred polyethyleneimines are linear polyethyleneimines, wherein x is from 8 to 1500, y is 0 and z is 2.

Preferred commercially available polyethylenimines are sold by BASF SE under the trademark Lupasol®, particularly Lupasol™ G100.

It is preferred to use polyethyleneimine and isocyanate compounds in a weight ratio of 1:1 to 1:5, especially 1:2 to 1:3, or in a dry weight ratio of 1:1 to 1:10, especially 1:4 to 1:6. These weight ratios provide resins having the highest encapsulation efficiency and therefore the most suitable for encapsulation.

In a process according to the present invention, formation of the shells around the droplets in step f) can be effected by heating. This can be achieved at a temperature of at least 50° C., preferably at least 60° C., more preferably in a range of from 70° C. to 90° C. and in particular 75° C. to 85° C., in order to ensure sufficiently rapid reaction progress. It may be preferred to increase the temperature continuously or in stages (e.g. in each case by 5° C.) until the reaction is essentially complete. Afterwards, the dispersion may cool down to room temperature.

The reaction time typically depends on the nature of the reactive wall-forming materials, the amount of said materials employed, and the temperature used. The period of time for the reaction is ranging from a few minutes to several hours. Usually, microcapsule formation is effected between ca. 60 minutes to 6 h or up to 8 h at the temperatures defined above.

An important parameter of the composition prepared by a process according to the present invention is the volume average diameter of the microcapsules Dv(50). The microcapsules can have a volume average diameter Dv(50) of 0.1-500 μm, preferably 1-100 μm, even more preferably 5-30 μm. Microcapsules having diameters within the preferred ranges provide optimal balance between stability in and visual appearance of the product in which they are used, as well as a good deposition on various substrates.

For particular applications, a specific volume average diameter might be advantageous. For example, for rinse off hair conditioner, capsules with Dv(50) of 10-13 μm are preferred, due to better deposition of microcapsule having these diameters.

The volume average particle size of the microcapsules can be measured by light scattering measurements using a Malvern 2000S instrument and the Mie scattering theory. The principle of the Mie theory and how light scattering can be used to measure capsule size can be found, for example in H. C. van de Hulst, Light scattering by small particles, Dover, N.Y., 1981. The primary information provided by static light scattering is the angular dependence of the light scattering intensity which, in turn, is linked to the size and shape of the capsules. However, in a standard operation method, the size of a sphere having a size equivalent to the size of the diffracting object, whatever the shape of this object is, is calculated by the Malvern proprietary software provided with the apparatus. In case of polydisperse samples, the angular dependence of the overall scattering intensity contains information about the size distribution in the sample. The output is a histogram representing the total volume of capsules belonging to a given size class as a function of the capsule size, whereas an arbitrary number of 50 size classes is typically chosen.

Experimentally, a few drops of the dispersion containing about 10% of capsules are added to a circulating stream of degassed water flowing through a scattering cell. The angular distribution of the scattering intensity is measured and analyzed by Malvern proprietary software to provide the average size and size-distribution of the capsules present in the sample. In the context of the present invention, the percentiles Dv(10), Dv(50) and Dv(90) are used as characteristics of the capsule size distribution, wherein the Dv(10) value is the volume-average diameter at which 10% of the total droplets volume is comprised of droplets with a diameter less than this value, the Dv(50) value is the median droplet diameter of the volume distribution and corresponds to volume-average diameter at which 50% of the total droplet volume is comprised of droplets with a diameter less than this value, and Dv(90) value is the diameter at which 90 of the samples volume is comprised of droplets with a diameter less than this value. In context of the present invention the term "particle size" means indifferently "volume-average particle size" or "volume-average particle diameter".

A preferred embodiment is a process, wherein:
A target range for the volume average diameter of the droplets of the hydrophobic (discontinuous phase) of the resulting emulsion is pre-defined;
The actual volume average diameter of the droplets of the hydrophobic phase in the emulsion of the organic phase (II) in the aqueous phase (I) is determined;
The speed of the stirrer and/or the time of stirring of the mixture are adjusted until the target value volume average diameter of the droplets of the hydrophobic phase of the resulting emulsion is reached in order to obtain the pre-defined target volume average diameter of the droplets of the hydrophobic phase.

The cores of the microcapsules are typically 60 to 97% by weight and the shell of the microcapsule is typically 40 to 3% by weight, based on the total weight of the microcapsule, preferably the core is 70 to 95% by weight and the shell is 30 to 5% by weight, and in particular the core is 80 to 90% by weight and the shell is 20 to 10% by weight based on the total weight of the microcapsule.

The microcapsules can have a zeta potential at pH 4 of −100 to +100 mV, preferably −50 to +50 mV, even more preferably −10 to +40 mV. Dispersions of microcapsules having zeta potentials in the preferred range are less prone to phase separation than microcapsules outside of this preferred range.

The zeta potential can be measured using Zetasizer Nano Z. Before measurement, the capsules are preferably treated as follows:
A capsule dispersion is filtered off, washed 5 times with distilled water and re-dispersed again;

2 g of the dispersion is added to 8 g of a buffer solution at pH 4.

A laser with a wavelength of 633 nm is preferably used for the measurements.

In a process according to the present invention, the aqueous phase (I) can additionally comprise a cationic polymer. On one hand, cationic polymers are known to improve the deposition and rinse resistance of microcapsules on various substrates, such as fabrics, skin and hair. On the other hand, the cationic polymer can also act as a dispersion aid. Thus, the process according to the present invention can additionally comprise the step of:

Adding a cationic polymer.

The cationic polymer can be added after step c) and before step d), in which case the polymer may participate to both emulsion and shell formation and, for example, be entrapped physically in this shell.

The cationic polymer can be added after step d) and before step e).

The cationic polymer can be added after step e) and before step f).

The cationic polymer can be added during step f).

In those cases, the polymer may participate to shell formation and, for example, be entrapped physically in this shell.

The cationic polymer can be added after step f), in which case the polymer does not participate to the shell formation but possibly deposits on the shell surface.

The cationic polymer can be an ampholytic polymer. In the context of the present invention, an "ampholytic polymer" is to be understood as a polymer comprising both cationic and anionic groups, or comprising corresponding ionizable groups. The cationic ampholytic polymer comprises more cationic groups than anionic groups or groups that can form anions, and as such, has a net positive charge.

The ampholytic polymer can comprise from 1 to 99 mol % of cationic groups and from 1 to 99 mol % of anionic groups or groups than can form an anion. In a preferred embodiment of the present invention, the ampholytic polymer comprises 2 to 99 mol %, in particular 30 to 95 mol %, and more particularly 60 to 90 mol %, of cationic groups and 1 to 98 mol %, in particular 5 to 70 mol %, and more particularly 10 to 40 mol % of anionic groups or groups than can form an anion.

The cationic groups in the cationic polymer can be pH independent. The cationic groups in the cationic polymer can be quaternary ammonium groups.

The cationic polymer can be derived from at least one a monomer bearing quaternary ammonium functionality. In particular, the cationic monomer can be selected from the group consisting of quaternized dimethylaminoethyl acrylate (ADAME), quaternized dimethylaminoethyl methacrylate (MADAME), dimethyldiallyl ammonium chloride (DADMAC), acrylamidopropyltrimethylammonium chloride (APTAC) and methacrylamidopropyltrimethylammonium chloride (MAPTAC).

When the cationic polymer comprises anionic groups or groups that can form anions, it can be additionally derived from a monomer selected from the group consisting of acrylic based monomers, including acrylic acid, methacrylic acid, itaconic acid, crotonic acid, maleic acid, fumaric acid and strong-acid monomers, for example monomers with a sulfonic or a phosphonic acid-type function such as 2-acrylamido-2-methylpropane sulfonic acid, vinylsulfonic acid, vinylphosphonic acid, allylsulfonic acid, allylphosphonic acid, styrene sulfonic acid. The acrylic based monomer may also be any water-soluble salts of these monomers; wherein the salt is a salt of an alkali metal, an alkaline-earth metal or an ammonium. The most preferred acrylic based monomer is acrylic acid, methacrylic acid, or a water soluble salt thereof.

The cationic polymer can further be additionally derived from a non-ionic monomer selected from the group consisting of water soluble vinyl monomers, more particularly acrylamide, methacrylamide, N-isopropylacrylamide, N,N-dimethylacrylamide, N-methylolacrylamide, N-vinylformamide, N-vinyl acetamide, N-vinylpyridine and/or N-vinylpyrrolidone.

The cationic polymer can be an ampholytic co-polymer derived from a cationic monomer or a monomer that can form cations, in particular containing at least one quaternary ammonium group, an anionic monomer or a monomer that can form anions, in particular based on acrylic acid, methacrylic acid or a derivative thereof, and optionally a non-ionic monomer. Such polymers offer an optimal combination of being compatible with the shell, having good dispersion efficiency, good flow properties and excellent affinity with the various substrates hereinabove mentioned.

In a more particular embodiment, the ampholytic co-polymer is a co-polymer of acrylic acid or methacrylic acid, and acrylamidopropyltrimethylammonium chloride (APTAC) or methacrylamidopropyltrimethylammonium chloride (MAPTAC), as for instance described in WO 2016/207180 A1.

In a still more particular embodiment, the ampholytic copolymer is a terpolymer formed from acrylic acid monomer, MAPTAC monomer and acrylamide monomer.

In a more preferred embodiment, the acrylic acid/MAPTAC copolymer, and more particularly the terpolymer, is formed by reacting 1 to 2 molar equivalents of acrylic acid monomer with 4 molar equivalents of the MAPTAC monomer, more particularly 1 molar equivalent of acrylic acid monomer to 4 molar equivalents of MAPTAC monomer (for example Floset CAPS 371L), and still more particularly 1.6 molar equivalents of acrylic acid monomer to 4 molar equivalents of MAPTAC monomer.

Although, in the context of the present invention, Floset CAPS 371L is a preferred cationic polymer, it can also be replaced by any other acrylic acid/MAPTAC copolymer described in the previous paragraph. Another preferred cationic polymers based on MAPTAC/acrylamide is Salcare SC60, commercialized by BASF. In an embodiment of the invention the copolymer has a molecular weight of at least 100'000 g/mol, and more particularly at least 500'000 g/mol.

Polymers with lower molecular weight do not provide the desired performance, while polymers having higher molecular weight increase the viscosity of both emulsion and microcapsule dispersions to a too large extent.

The ampholytic polymer may be employed in an encapsulated fragrance composition according to the present invention in an amount from 1 to 20 wt %, more particularly 2 to 10 wt %, based on the weight of the composition.

The ampholytic polymer can be prepared using polymerization techniques that are well known to a person skilled in the art. These known polymerization techniques include solution polymerization, gel polymerization, precipitation polymerization, inverse emulsion polymerization, aqueous emulsion polymerization, suspension polymerization and micellar polymerization.

The ampholytic polymer can be structured by at least one structuring agent, which may be chosen from the group consisting of polyethylenically unsaturated monomers (having at least two unsaturated functional groups such as for example vinyl, allyl and acryl) and compounds having epoxy functional groups. For instance, such structuring agents can include methylene bisacrylamide (MBA), triallyamine and polyethylene glycol diacrylate. Alternatively, macro initiators such as polyperoxides, polyazo compounds and polytransfer agents such as polymercaptan polymers can be used.

As mentioned herein above, in a process according to the present invention, the organic phase (II) comprises at least one fragrance ingredient. The fragrance ingredient may be selected from any of those fragrance ingredients described in S. Arctander, Fragrance and Flavor Chemicals, 1969, Montclair, N.J., USA.

Fragrance retention during microcapsule formation, as well as stability towards leakage once a capsule is formed, is promoted through the use of high amounts of fragrance ingredients having a relatively high C log P. In particular, at least about 50%, more particularly more than about 60%, and still more particularly more than about 80% of ingredients should have a C log P of about 2.5 or greater, and more particularly 3.3 or greater, and still more particularly 4.0 or greater. Use of such fragrance ingredients is regarded as helpful in reducing diffusion of fragrance through a microcapsule shell and into a consumer product base under specific time, temperature, and concentration conditions.

The values of C log P of fragrance ingredients have been reported in many databases, including the Pomona 92 database, available from Daylight Chemical Information Systems, Inc., Daylight CIS, Irvine, Calif.

In addition to fragrance ingredients, solvents may be employed in the microcapsules of the present invention. Solvents are hydrophobic materials that are miscible with the fragrance ingredients, and which have little or no odor in the quantities employed. Solvents commonly employed have high C log P values, for example greater than 6 and even greater than 10. Solvents include triglyceride oil, mono and diglycerides, mineral oil, silicone oil, diethyl phthalate, polyalpha olefins, castor oil and isopropyl myristate.

However, it is also possible to employ substantially no solvent material in the core of the microcapsules. Indeed, it was found that it is possible to prepare an encapsulated fragrance composition wherein the microcapsule core is composed entirely of fragrance ingredients and no solvent. Solvent-free encapsulated fragrances may be employed, in particular, when the fragrance ingredients making up the core material have limited water solubility. In particular, the core material should be formed with a large proportion of fragrance ingredients having a solubility in water of 15,000 ppm or less, more particularly 5000 ppm or less, and still more particularly 3000 ppm or less. More particularly, at least 60%, more particularly at least 70% and still more particularly at least 80% of fragrance ingredients should have a solubility in water of 15,000 ppm or less, more particularly 5000 ppm or less, and still more particularly 3000 ppm or less. Avoiding the use of a solvent in the microcapsule core is generally advantageous in terms of reducing costs and having regard to the environmental considerations.

The process according to the present invention can comprise the additional step of:

Drying the plurality of microcapsules dispersed in the dispersion medium to provide microcapsules in a solid form.

The process is then for preparing an encapsulated fragrance composition, the composition comprising a plurality of microcapsules is solid form. In context of the present invention, drying means removal of the dispersion medium. The core material of the microcapsules still remains encapsulated. That means the dried microcapsules comprise at least one fragrance ingredient.

The microcapsules or dispersions of microcapsules may be dried using techniques known in the art. For example, the solid capsules can be isolated by filtration and dried. Drying of the isolated capsules may be performed by heating, e.g. in an oven or by contact with a heated gas stream.

Preferably, drying of the dispersion is carried out by spray drying or fluid-bed drying.

Spray drying techniques well known in the art. A spray-drying process pushes suspended capsules through a nozzle and into a drying chamber. The capsules may be entrained in a fluid (such as air) that moves inside of a drying chamber. The fluid (which may be heated, for example at a temperature of 150 and 120° C., more preferably between 170° C. and 200° C., and still more preferably between 175° C. and 185° C.) causes the liquid to evaporate, leaving behind the dried capsules which can then be collected from the process equipment and further processed.

It is conventional to mix spray dried capsules with flow aids to produce a flowable powder that are not susceptible to caking. Flow aids include silicas or silicates, such as precipitated, fumed or colloidal silicas; starches; calcium carbonate; sodium sulphate; modified cellulose; zeolites; or other inorganic particulates known in the art.

It is quite common, given the high temperatures and impaction forces encountered during a spray drying procedure, for core shell capsules to lose some of their core material.

Furthermore, it may not be possible to work at sufficiently high temperatures for a sufficiently long period of time to drive off all moisture from the dispersion, without compromising the thermal stability of the capsules. Accordingly, the polyurea or polyurethane capsules emerging from a spray-drying process, as herein described, may contain small amounts of surface oil as well as residual moisture.

If the microcapsules of the present invention are intended to be stored in the form of dispersion, the pH of the dispersion can be adjusted to a level of about 5 to 10. This may be achieved with the addition to an alkaline dispersion of a suitable acid, such as citric acid or formic acid.

A microcapsule dispersion can be prepared continuously or batchwise, preferably batchwise.

The dispersion of the microcapsules may contain non-encapsulated, i.e. free fragrance ingredients, external of the capsules in the aqueous dispersion.

A further aspect of the present invention refers to the use of an anionically modified polyisocyanate as a dispersion aid in a process for preparing an encapsulated fragrance composition. This use can have the optional features as outlined herein above with respect to the process according to the present invention.

The present invention also refers to an encapsulated fragrance composition obtainable by a process as outlined herein above. Generally such a composition shows a good deposition and adherence of microcapsules on a substrate in order to assure the benefit of these capsules in the area of personal care, home care, industrial or institutional or hospital applications, material protections, pharmaceutical industry or plant protection.

Furthermore, the present invention relates to a consumer product comprising such an encapsulated fragrance composition, in particular a personal care product, a home care product, or a laundry care product.

Further advantages and particular features of the present invention become apparent from the following discussion of several examples.

Example 1: Capsule Synthesis with Poly(Vinylpyrrolidone) as Dispersion AID

An aqueous solution of 130 g of polyvinylpyrrolidone (PVP K60, ex Ashland), 6 g hydrodispersible isocyanate based on hexamethylene diisocyanate (Bayhydur® XP 2547, ex Covestro) and 450 g water was prepared and the pH was adjusted to 9 using buffer salts. 300 g of fragrance to be encapsulated was mixed with the aqueous phase. 25 g of diisocyanate 4,4 dicyclohexylmethanediyle (Desmodur® W1, ex Covestro) was added to this mixture. The resulting mixture was emulsified at room temperature by means of a stirring device. The emulsification process was carried out to the desired droplet size. Then 10 g of polyethyleneimine solution (Lupasol® G100, ex BASF, as purchased) was added in one step. The mixture was heated gradually to 80° C. for 4 h. After the polymerization, 18 g of ammonia solution and 3 g of hydroxyethylcellulose (Natrosol 250HX, ex Ashland) were added. The mixture was then cooled down to room temperature.

An encapsulated fragrance composition was obtained. The volume average capsule size distribution, obtained with light scattering measurements using a Malvern 2000S instrument, was D(50)=16 μm and D(90)=30 μm. The Zeta potential was −5 mV.

Example 2: Comparative Example to Example 1 with the Isocyanates in the Organic Phase (Not According to the Present Invention)

An aqueous solution of 130 g of polyvinylpyrrolidone (PVP K60, ex Ashland was prepared and the pH was adjusted to 9 using buffer salts. A mixture comprising 300 g fragrance to be encapsulated, 20 g Desmodur® W1 and 8 g Bayhydur® XP 2547 was prepared. The aqueous phase and the organic phase were combined and emulsified at room temperature by means of a stirring device. The emulsification process was carried out to the desired droplet size. Then 10 g of polyethyleneimine solution (Lupasol® G100, ex BASF, as purchased) was added in one step. The mixture was heated gradually to 80° C. for 4 h. After the polymerization, 18 g of ammonia solution and 3 g hydroxyethylcellulose (Natrosol™ 250HX, ex Ashland) were added. The mixture was then cooled down to room temperature.

An encapsulated fragrance composition was obtained. The volume average capsule size distribution, obtained with light scattering measurements using a Malvern 2000S instrument, was D(50)=20 μm and D(90)=40 μm with a shell weight. The Zeta potential was −5 mV.

Example 3: Capsule Synthesis with Poly(Vinylpyrrolidone) as Dispersion Aid and Cationic Terpolymer as Deposition Agent An aqueous solution of 130 g of polyvinylpyrrolidone (PVP K60, ex Ashland), 6 g hydrodispersible isocyanate based on hexamethylene diisocyanate (Bayhydur® XP 2547, ex Covestro) and 450 g water was prepared and the pH was adjusted to 9 using buffer salts. 300 g of fragrance to be encapsulated was mixed with the aqueous phase. 25 g of diisocyanate 4,4 dicyclohexylmethanediyle (Desmodur® W1, ex Covestro) was added to this mixture. The resulting mixture was emulsified at room temperature by means of a stirring device. The emulsification process was carried out to the desired droplet size. Then 10 g of polyethyleneimine solution (Lupasol® G100, ex BASF, as purchased) was added in one step. The reaction mixture was heated gradually to 60° C.) and an aqueous solution of 30 g of a solution of copolymer of methacrylamidopropyltrimethylammonium chloride and acrylic acid (Floset™ DP CAPS 371L, ex SNF, as supplied at 26.5 wt % in water) was added. Then, the reaction mixture was further heated to 80° C. for 2 h. Thereafter, 18 g of ammonia solution and 3 g hydroxyethylcellulose (Natrosol™ 250HX, ex Ashland) were added. The mixture was then cooled down to room temperature.

An encapsulated fragrance composition was obtained. The volume average capsule size distribution, obtained with light scattering measurements using a Malvern 2000S instrument, was D(50)=10 μm and D(90)=30 μm. The Zeta potential was +5 mV.

Example 4: Comparative Example to Example 3 with the Isocyanates in the Organic Phase (Not According to the Present Invention)

An aqueous solution of 130 g of polyvinylpyrrolidone (PVP K60, ex Ashland) and 450 g water was prepared and the pH was adjusted to 9 using buffer salts. A mixture comprising 300 g fragrance to be encapsulated, 20 g Desmodur® W1 and 8 g Bayhydur® XP 2547 was prepared. The aqueous phase and the organic phase were combined and emulsified at room temperature by means of a stirring device. The emulsification process was carried out to the desired droplet size. Then 10 g of polyethyleneimine solution (Lupasol® G100, ex BASF, as purchased) was added in one step. The reaction mixture was heated gradually to 60° C. and an aqueous solution of 30 g copolymer of methacrylamidopropyltrimethylammonium chloride and acrylic acid (Floset™ CAPS 371L, ex SNF, as supplied at 26.5 wt % in water) was added. Then, the reaction mixture was further heated to 80° C. for 2 h. Thereafter, 18 g of ammonia solution and 3 g hydroxyethylcellulose (Natrosol™ 250HX, ex Ashland) were added. The mixture was then cooled down to room temperature.

An encapsulated fragrance composition was obtained. The volume average capsule size distribution, obtained with light scattering measurements using a Malvern 2000S instrument, was D(50)=20 μm and D(90)=40 μm. The solid content of the slurry was 45 wt %. The Zeta potential was +5 mV.

Example 5: Capsule Synthesis with Cationic Copolymer as Templating Agent and the Isocyanates in the Aqueous Phase An aqueous solution of 100 g of a copolymer of methacrylamidopropyltrimethylammonium chloride and acrylic acid (Floset™ DP CAPS 371L, ex SNF, as supplied at 26.5 wt % in water), 6 g hydrodispersible isocyanate based on hexamethylene diisocyanate (Bayhydur® XP 2547, ex Covestro) and 450 g water was prepared and the pH was adjusted to 9 using buffer salts. 300 g of fragrance to be encapsulated was mixed with the aqueous phase. 25 g of diisocyanate 4,4 dicyclohexylmethanediyle (Desmodur® W1, ex Covestro) was also added to this mixture. The resulting mixture was emulsified at room temperature by means of a stirring device. The emulsification process was carried out to the desired droplet size. Then 10 g of polyethyleneimine solution (Lupasol® G100, ex BASF, as purchased) was added in one step. The mixture was heated gradually to 80° C. for 4 h. After the polymerization, 18 g of ammonia solution and 10 g of a cationic acrylamide (Flosoft™ FS555, ex SNF) were added. The mixture was then cooled down to room temperature.

An encapsulated fragrance composition was obtained. The volume average capsule size distribution, obtained with light scattering measurements using a Malvern 2000S instrument, was D(50)=10 µm and D(90)=30 µm. The Zeta potential (mV) was +30 mV.

Example 6: Comparative Example to Example 5 with the Isocyanates in the Organic Phase (Not According to the Present Invention)

An aqueous solution of 100 g a copolymer of methacrylamidopropyltrimethylammonium chloride and acrylic acid (Floset™ DP CAPS 371L, ex SNF, as supplied at 26.5 wt % in water) and 450 g water was prepared and the pH was adjusted to 9 using buffer salts. A mixture comprising 300 g fragrance to be encapsulated, 20 g Desmodur® W1 and 8 g Bayhydur® XP 2547 was prepared. The aqueous phase and the mixture were combined and emulsified at room temperature by means of a stirring device. The emulsification process was carried out to the desired droplet size. Then 10 g of polyethyleneimine solution (Lupasol® G100, ex BASF, as purchased) was added in one step. The reaction mixture was heated gradually to 80° C. for 4 h. After the interfacial polymerization, 18 g of ammonia solution and 0.4 g Natrosol™ 250HX were added. The mixture was then cooled down to room temperature.

An encapsulated fragrance composition was obtained. The volume average capsule size distribution, obtained with light scattering measurements using a Malvern 2000S instrument, was D(50)=10 µm and D(90)=30 µm. The solid content of the slurry was 45 wt %. The Zeta potential (mV) was +38 mV.

Example 7: Influence of Process on the Stability of the Microcapsules with Respect to Leakage in a Model Extractive Medium The model extractive medium was a system consisting of 1.8 ml of an aqueous solution of ethanol at an initial concentration of 20 vol % co-existing with 10 ml of an un-miscible cyclohexane phase.

The slurry to be assessed was diluted in such a way that the fragrance concentration in the diluted slurry is about 10 wt % and 200 microliters of this diluted slurry are added to the vial.

The vial was submitted to a horizontal mixing on an elliptic horizontal x,y-mixing equipment operating at a 250 rpm for 4 hours (shaking in the z direction is avoided).

The upper cyclohexane phase containing the extracted fragrance was analysed spectrophotometrically by using a UV/visible light spectrometer. The fragrance concentration was determined by measuring the intensity of the absorbed UV/visible light at the maximum absorbance wavelength, which had been determined previously by using a reference fragrance/cyclohexane solution of known concentration. This latter reference solution was used as an external standard for the quantification of the extracted fragrance. The leakage value is defined as the percentage of the encapsulated fragrance that has been recovered in the hexane phase.

Representative leakage values are given in Table 1 hereunder.

TABLE 1

Leakage values for different encapsulated fragrance compositions

| Example | Leakage in model extractive medium |
|---|---|
| Example 1 | 22 +/- 8 wt % |
| Example 2 (comparative) | 70 wt % |
| Example 3 | 33 +/- 17 wt % |
| Example 4 (comparative) | 70 wt % |
| Example 5 | 55 +/- 5 wt % |
| Example 6 (comparative) | 70 wt % |

From Table 1 it can be seen that adding the polyisocyanates in the aqueous phase instead of pre-dissolving them in the organic (fragrance) phase improves the stability of the microcapsules with respect to leakage in a model extractive medium.

Example 8: Influence of Process on the Olfactive Performance of the Microcapsules The microcapsules were incorporated in a standard, unfragranced liquid fabric care conditioner stored for one month at 37° C. and 45° C. The amount of microcapsule in the conditioner was 0.5 wt %.

35 g of the base was used in a side-loaded wash machine (20 L capacity, loaded with 1 kg terry towelling, preferably washed beforehand with an unfragranced laundry detergent); a rinse cycle was performed at a temperature of 20° C., followed by spin drying.

In both laundry rinse and wash cases, the pre-rub olfactive evaluation was performed on wet laundry directly out of the machine and after 4 hours. For this evaluation, the terry towelling was handled carefully in order minimize the risk of breaking the microcapsules mechanically. The post-rub olfactive evaluation was performed after line drying the terry towelling for 24 hours at room temperature. This evaluation was performed by gently rubbing one part of the terry towelling on another part of same terry towelling. The olfactive performance (intensity) has been assessed by a panel of 4 experts rated on a scale of 1-5 (1=barely noticeable, 2=weak, 3=medium, 4=strong and 5=very strong). When relevant, qualitative comments on the perceived odour direction were recorded.

The results of the olfactive performance assessment are reported on Table 2.

TABLE 2

Olfactive score on dry towel (after 24 hours drying at room temperature)

| | Olfactive performance after 2 months at 37° C. | | Olfactive performance after 2 weeks at 45° C. | |
|---|---|---|---|---|
| Example | Pre-rub score | Post-rub score | Pre-rub score | Post-rub score |
| Example 3 | 2 | 3 | 2 | 3 |
| Example 4 (comparative) | 2 | 3 | 2 | 3 |
| Example 5 | 1.2 | 1.3 | 0.8 | 1.1 |
| Example 6 (comparative) | 0.7 | 0.5 | 0 | 0 |

From Table 2 it can be seen that adding the polyisocyanates in the aqueous phase instead of pre-dissolving them in the organic (fragrance) phase has no negative impact on the olfactive performance of the samples after storage. The olfactive stability may even be improved, as in the case of Example 5 vs. Example 6.

Example 9: Surface Tension

The surface tension of aqueous phases comprising various water-dispersible anionically modified isocyanates and/or stabilizing polymers was measured. The measurement was performed by using the so-called pendant drop method. The instrument used was a Drop Shape Analyzer-DSA30 manufactured by Krüss GmbH, Hamburg, Germany. The way the surface tension is calculated by the instrument software is described in Krüss Technical Note TN316e, dated October 2010 and available, for example, under:

https://www.kruss-scientific.com/fileadmin/user_upload/website/literature/kruss-tn316-en.pdf

TABLE 3

| Surface tension | |
|---|---|
| Aqueous phase composition | Surface tension [mN/m] |
| 13 wt % poly(vinylpyrrolidone) (PVP) K 60 | 67.7 +/− 0.3 |
| 13 wt % PVP K 60 + 6 wt % Bayhydur ™ XP2547 | 55.8 +/− 0.3 |
| 10 wt % Floset ™ DP CAPS 371L | 51.3 +/− 0.3 |
| 10 wt % Floset ™ DP CAPS 371L + 5 wt % Bayhydur ™ XP2547 | 47.6 +/− 0.2 |

From Table 3 it can be seen that adding the polyisocyanates in the aqueous phase comprising a stabilizing polymer decreases the surface tension of this aqueous phase. Without being bound by theory, these results support that polyisocyanates added in the water phase are located on the water side of the water/oil interface, where they participate to the emulsification process and are more available for further reaction with the polyamines during the microcapsule formation.

The surface tension results show that the addition of bayhydur XP2547 in the aqueous phase helps to control the particle size of the emulsion, forming smaller particle size (ex 10 μm vs 20 μm).

The invention claimed is:

1. A process of preparing an encapsulated fragrance composition, the composition comprising a plurality of microcapsules dispersed in a dispersion medium, the microcapsules comprising a core and a shell around the core, the process comprising the consecutive steps of:
   a) providing an aqueous phase (I) comprising at least one anionically modified polyisocyanate (A);
   b) providing an organic phase (II) comprising at least one fragrance ingredient;
   c) mixing the aqueous phase (I) and the organic phase (II) to obtain a mixture;
   d) forming an emulsion comprising droplets of the organic phase (II) in the continuous aqueous phase (I);
   e) adding at least one polyfunctional amine;
   f) effecting formation of shells around the droplets formed in step d), to obtain a dispersion of microcapsules; and, wherein the process comprises the additional step of:
   adding a polyisocyanate (B), which is different from polyisocyanate (A).

2. The process according to claim 1, wherein polyisocyanate (B) is added during step c).

3. The process according to claim 1, wherein polyisocyanate (B) is added after step c) and before step d).

4. The process according to claim 1, wherein polyisocyanate (B) is added during step d).

5. The process according to claim 1, wherein the anionically modified polyisocyanate (A) is according to Formula (1).

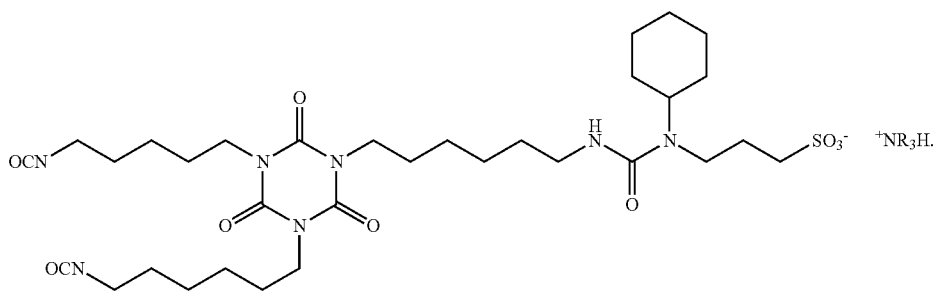

Formula (1)

6. The process according to claim 1, wherein the aqueous phase (I) provided in step a) additionally comprises a dispersion aid different from anionically modified polyisocyanate (A).

7. The process according to claim 1, wherein polyisocyanate (B) is a non-ionic polyisocyanate.

8. The process according to claim 7, wherein the non-ionic polyisocyanate is selected from the group consisting of dicyclohexylmethane diisocyanate, hexamethylene diisocyanate and isophorone diisocyanate.

9. The process according to claim 1, wherein the polyfunctional amine is a polyethyleneimine containing the following repeat units

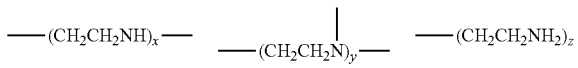

wherein
x is from 8 to 1500;
y is from 0 to 10; and
z is 2+y.

10. The process according to claim 1, wherein the aqueous phase (I) additionally comprises a cationic polymer.

11. The process according to claim 1, additionally comprising the step of:
adding a cationic polymer.

12. The process according to claim 10, wherein the cationic polymer is an ampholytic co-polymer derived from a cationic monomer or a monomer that can form cations and an anionic monomer or a monomer that can form anions.

13. An encapsulated fragrance composition obtainable by a process according to claim 1.

14. A consumer product comprising an encapsulated fragrance composition according to claim 13.

15. The process according to claim 6, wherein the dispersion aid different from anionically modified polyisocyanate (A) is a non-ionic dispersion aid.

16. The process according to claim 12, wherein the cationic monomer is a monomer containing at least one quaternary ammonium group.

17. The process according to claim 12, wherein the anionic monomer or the monomer that can form anions is based on a compound selected from the group consisting of: acrylic acid, methacrylic acid and derivatives thereof.

18. The process according to claim 12, wherein the cationic polymer is additionally derived from a non-ionic monomer.

19. The consumer product according to claim 14 selected from the group consisting of a personal care product, a home care product and a laundry care product.

* * * * *